United States Patent [19]

Kaufman et al.

[11] 4,057,052

[45] Nov. 8, 1977

[54] BLOOD-GAS SYRINGE

[75] Inventors: Joseph Kaufman, Emerson; Alois G. Prais, Garfield, both of N.J.

[73] Assignee: Becton, Dickinson and Company, Rutherford, N.J.

[21] Appl. No.: 735,162

[22] Filed: Oct. 26, 1976

[51] Int. Cl.$^2$ .............................................. A61B 5/00
[52] U.S. Cl. ............................. 128/2 F; 128/DIG. 5; 128/218 P
[58] Field of Search ............... 128/2 F, DIG. 5, 215, 128/218 P, 218 PA, 218 M, 218 R, 220, 221, 213, 214, 234

[56] References Cited

U.S. PATENT DOCUMENTS

| 718,979 | 1/1903 | Campbell | 128/218 P |
|---|---|---|---|
| 2,666,434 | 1/1954 | Ogle | 128/218 P |
| 3,985,122 | 10/1976 | Topham | 128/2 F |

FOREIGN PATENT DOCUMENTS 1,500,009  9/1967  France .............................. 128/218 P

*Primary Examiner*—John D. Yasko
*Attorney, Agent, or Firm*—Kane, Dalsimer, Kane, Sullivan and Kurucz

[57] ABSTRACT

The disclosure is of an improved blood gas syringe. In one embodiment, the improved syringe comprises a conventional syringe barrel, a plunger and an elastomeric piston at the bottom of the plunger. The plunger extends through and beyond the piston a short distance. The extended portion of the plunger, which is incompressible, serves as a stop means to prevent the piston from being compressed at the bottom of the barrel and to provide a chamber to hold a liquid anti-coagulant. The improved syringe has several advantages over prior art blood gas syringes, such as the obviation of inadvertently drawing air back into the syringe when pressure on the plunger is removed.

5 Claims, 4 Drawing Figures

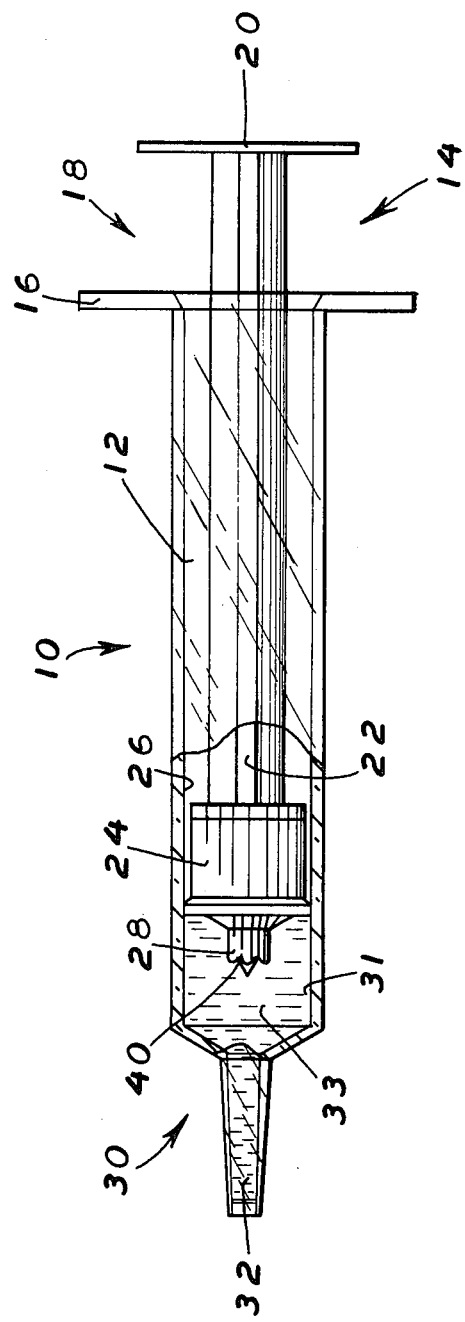

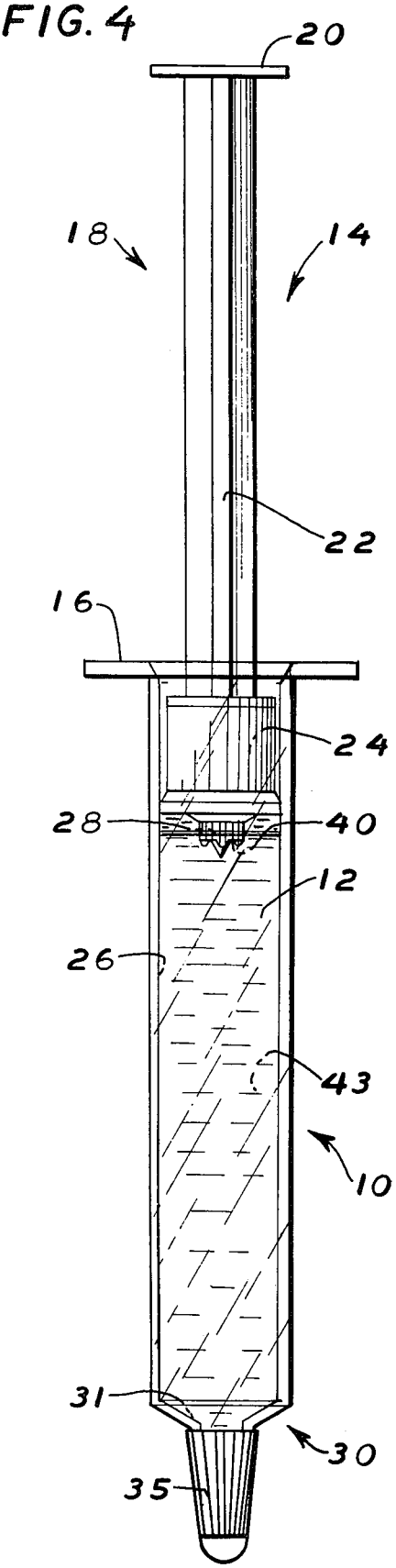
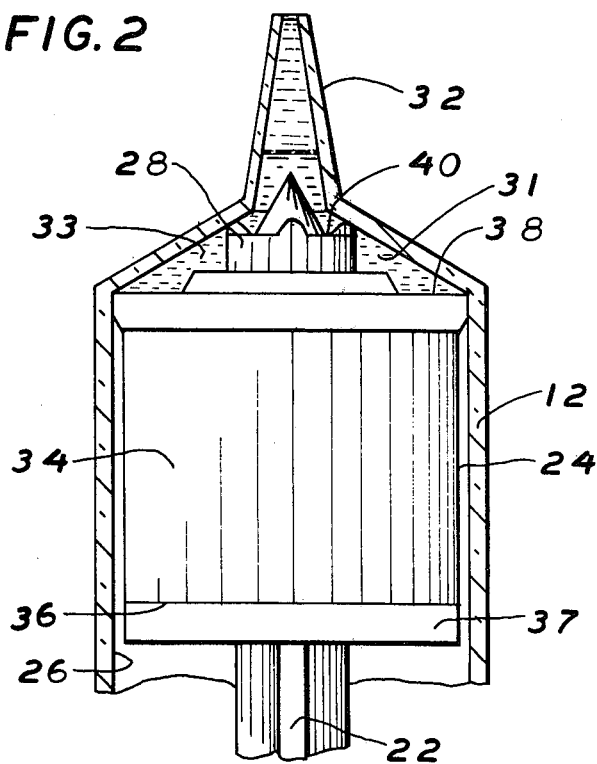
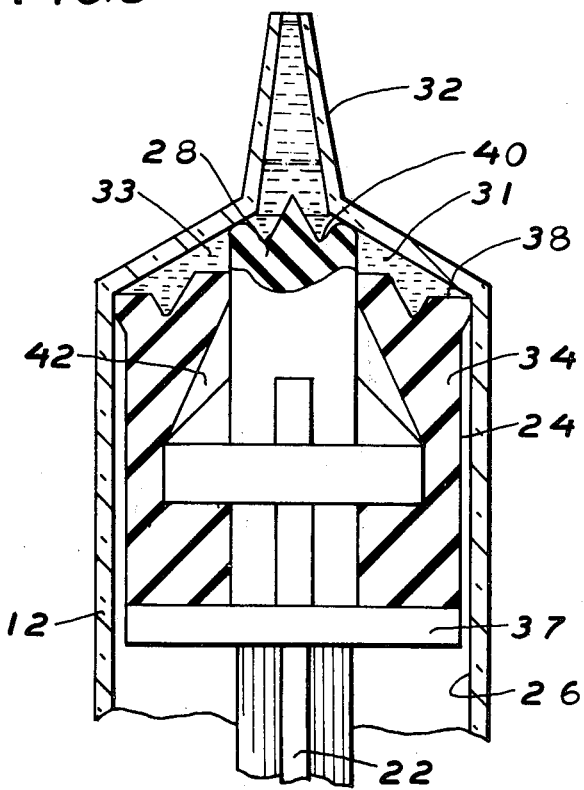

BLOOD-GAS SYRINGE

BACKGROUND OF THE INVENTION

1. Field of the Invention

The invention relates to syringes and more particularly to an improved blood gas syringe.

2. Brief Description of the Prior Art

The prior art is replete with descriptions of syringes and their construction; see for example U.S. Pat. Nos. 2,869,543; 3,076,456, and 3,570,486. In spite of the highly developed state of the art a number of problems have heretofore been associated with the available syringes, particularly blood gas syringes. For example, often when expelling a "filler" material from a syringe, by exerting pressure on the plunger, there is a "rebound" of the plunger when pressure is terminated. This is undesirable, particularly for a blood gas collecting syringe, because it will serve to draw air back into the syringe thereby contaminating the blood specimen being collected.

The improved syringe of the invention cannot inadvertently "rebound". In addition, in the preferred syringes of the invention, arterial pressure is sufficient to activate the withdrawal of the plunger as an aid indicating when an artery has been entered.

SUMMARY OF THE INVENTION

The invention comprises a syringe, which comprises; a cylindrical barrel having a first open end for receiving a plunger and a second open end adapted to mount a needle on the opening thereof; and a plunger slidably mounted in said barrel, said plunger being withdrawable from said barrel through said first open end and said plunger comprising (a) means for receiving a force to move said plunger in or out of said barrel, (b) an elastomeric piston adapted to form a sliding seal with the inner walls of said barrel, said piston having an upper end and a lower end and a bore therethrough communicating between said upper and lower ends, (c) a shank joining said means (a) to said piston, (d) an extension of said shank passing through said bore and extending beyond the lower end of said piston, said extension preventing the piston from contacting said second barrel end, (e) a chamber defined by said second open end of said barrel and the lower end of said elastomeric piston when said extension is in contact with said second open end; the entire surface of said piston lower end being in open communication with the inside of said barrel through said second open end; (f) an inert fluid disposed in said barrel between the second open end thereof and said piston, in a volume in excess of that required to fill said chamber and the bore of said needle.

The term "inert fluid" as used throughout the specification and claims means a fluid which is inert in respect to adversely affecting a blood specimen upon which gas analysis is desired. Representative of inert fluids are anti-coagulants such as liquid solutions of sodium heparin, sodium citrate and the like.

The syringes of the invention are useful as "blood gas" syringes; i.e. they are useful for collecting blood specimens which will be subjected to gas analysis.

BRIEF DESCRIPTION OF THE DRAWINGS

FIG. 1 is a cross-sectional in part side elevation of an embodiment syringe of the invention.

FIG. 2 is an enlarged view of a part of the embodiment syringe seen in FIG. 1 but after ejection of an excess of inert fluid.

FIG. 3 is a cross-sectional side elevation of the component shown in FIG. 2.

FIG. 4 is an isometric view of the embodiment syringe of FIG. 1 shown after use to collect a blood specimen.

DETAILED DESCRIPTION OF THE INVENTION

Representative of the syringes of the invention is the syringe 10, a cross-sectional in part view of which may be seen in FIG. 1. The syringe 10 comprises a barrel 12 having an open end 14. Disposed about the periphery of open end 14 is finger hub 16 which facilitates holding syringe 10 during operation of plunger 18 which is shown slidably mounted in barrel 12. The plunger 18 comprises a handle 20 which functions as a means for receiving a digital force to move the plunger 18 in or out of barrel 12 and a shank 22. Shank 22 connects the handle 20 to an elastomeric piston 24 which forms a sliding seal within side wall 26 of barrel 12. An extension 28 of shank 22 traverses the center of piston 24 through a bore 42 (not seen in FIG. 1) and serves as a stop to prevent piston 24 from contacting fully the end 30 of barrel 12, thus creating a chamber 31 between piston 24 and end 30 (see FIG. 2 for further details). As shown in the FIG. 1, the chamber 31 is partially filled with an inert fluid 33. The volume of the inert fluid 33 is in excess of that required to fill the chamber 31 when plunger 18 is thrust forward into its forwardmost position. The excess is also sufficient to fill the bore of needle hub 32 and any needle mounted thereon. The end 30 is partially closed to restrict the opening therein and is adapted to mount a needle on needle hub 32 so that a needle bore (not shown) will be co-axially aligned with the opening in open end 30.

Further details of the structure of the syringe 10 may be seen in FIG. 2, an enlarged view of a part of the plunger component 18 but after ejection of excess inert fluid 33 by moving plunger 22 inward so piston 24 is in its most forward position. This leaves chamber 31 filled with the inert fluid 33 and free of air. It also leaves the bore of needle hub 32 and any needle mounted thereon filled with inert fluid 33, free of air. As seen in FIG. 2, the piston 24 has a central body portion 34, an upper end 36 supported by a base plate 37 part of shank 22 and a lower end 38. The central body 34 has a diameter less than the diameter of the inside of barrel 12 so that there is no physical engagement between piston 24 and the inner walls 26. End 38 has an expanded diameter to form a sealing flange to mate and seal with walls 26. In the extension 28 there are channels 40. The channels or grooves 40 traverse extension 28 so that when extension 28 is held against the end 30 of barrel 12, open communication between the surface of the lower end 38 of the piston 24 and the inside of barrel 12 through hub 32 is not interrupted by extension 28 blocking the opening into hub 32. This is important so that incoming pressure acts on the whole surface of lower end 38, permitting activation of the plunger by arterial pressure as will be described more fully hereinafter. Further details of the plunger 18 may be seen by referring now to FIG. 3, a cross-sectional side elevation of the view seen in FIG. 2. As shown in FIG. 3 the extension 28 is firmly supported by being integral with shank 28, traversing a central bore 42 through elastomeric piston 24. Thus, when extension 28 impinges on the end 30 of barrel 12, no pressure is put on piston 24 but is rather transmitted to shank 22. This obviates the problem of compressibility of the piston 24, which upon release would result in the "rebound phenomena" previously referred to as a prior art problem.

The syringe 10 may be fabricated from any material conventionally used to produce syringes. For example, the barrel, shank and extension may be made from metal, ceramic, glass, polymeric resin and like materials. The elastomeric piston may be fabricated from rubber, synthetic polymeric elastomers and like elastomeric materials.

The blood gas syringe 10 may be operated as follows. A needle is secured to hub 32 and plunger 18 is pressed into barrel 12 until extension 28 makes contact with end 30 of barrel 12. This action serves to expel the excess of inert fluid 33 and to carry with the expulsion any air which may have been in the bore of hub 32 and the needle mounted thereon. In this condition, air has been excluded from the blood receiving areas of the blood gas syringe 10. Because the resilient, compressible piston 24 has not been compressed against end 30, when the operator's finger is removed from the handle 20 of plunger 18, there will be no rebound to draw air back into the needle bore, hub 32 bore or chamber 31. The operator then gains entry into a mammalian blood vessel using conventional venipuncture technique. If entry has been made into an artery, the arterial pressure will force blood into the needle and because of the light interference fit of piston 24, will force the plunger 18 out of end 14 of barrel 12. This signals to the operator that an artery has been entered (note if the operator was seeking a vein, he or she can then withdraw the needle). Blood flowing into the needle bore and into hub 32 bore initially enters chamber 31 to admix with the inert fluid 33. Flow of the blood into chamber 31 through the channels 40 and extension 28 is readily made. The extension 28 does not block communication between the bore of hub 32 and chamber 31 because of the channels 40. Blood may then be withdrawn into the interior of barrel 12 by withdrawing of the plunger 18 either automatically as described above or by manual operation. When a desired amount of blood is obtained in the barrel 12, the connection with the mammalian blood vessel is terminated in the conventional manner by withdrawal of the needle. The needle may then be removed and needle hub 32 covered with a cap 35 as shown in FIG. 4, an isometric view of the embodiment syringe 10 following its filling with a blood specimen. This blood specimen 43 will have been collected without exposure of the blood to atmospheric gases in the environment and will be maintained isolated from the atmosphere. To ensure such isolation, it is preferable that the cap 35 be a hermetically sealing cap.

All of the above operative description presupposes that those skilled in the art will appreciate that good venipuncture and sterile technique should be followed.

What is claimed:

1. A syringe, which comprises;
    a cylindrical barrel having a first open end for receiving a plunger and a second open end adapted to mount a needle on the opening thereof; and
    a plunger slidably mounted in said barrel, said plunger being withdrawable from said barrel through said first open end and said plunger comprising;
    a. means for receiving a force to move said plunger in or out of said barrel,
    b. an elastomeric piston adapted to form a sliding seal with the inner walls of said barrel, said piston having an upper end and a lower end and a bore therethrough communicating between said upper and lower ends,
    c. a shank joining said means (a) to said piston (b);
    d. an extension of said shank passing through said bore and extending beyond the lower end of said piston, said extension preventing the piston from contacting said barrel second end;
    e. a chamber defined by said second open end of said barrel and the lower end of said piston when said extension is in contact with said second open end;
    f. an inert fluid disposed in said barrel between the second open end thereof and said piston, in a volume in excess of that required to fill said chamber and the bore of said needle;
    said extension having means thereon to permit the entire surface of said piston lower end being in open communication with the outside of said barrel through said second open end when said extension is in contact with said second open end.

2. The syringe of claim 1 wherein said means for receiving a force is a handle.

3. The syringe of claim 1 wherein said piston comprises a central body having a smaller diameter than the inside diameter of said barrel and an expanded end adapted to form a sliding seal with the inner walls of the barrel.

4. The syringe of claim 1 wherein said shank is integral with said extension and supports said extension.

5. The syringe of claim 1 wherein there is a chamber between the lower end of said piston and the second end of said barrel.

* * * * *